US00PP25140P3

(12) United States Plant Patent
Beckman

(10) Patent No.: US PP25,140 P3
(45) Date of Patent: Dec. 2, 2014

(54) ***EUCOMIS* PLANT NAMED 'GSALIPOL'**

(50) Latin Name: ***Eucomis vandermerwei*×*Eucomis hybrida***
Varietal Denomination: GSALIPOL

(71) Applicant: Golden State Bulb Growers, Inc., Moss Landing, CA (US)

(72) Inventor: Peter M. Beckman, Santa Cruz, CA (US)

(73) Assignee: Golden State Bulb Growers, Inc., Moss Landing, CA (US)

( * ) Notice: Subject to any disclaimer, the term of this patent is extended or adjusted under 35 U.S.C. 154(b) by 112 days.

(21) Appl. No.: 13/694,460

(22) Filed: Dec. 4, 2012

(65) Prior Publication Data

US 2014/0157469 P1 Jun. 5, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Barbara Campbell; Cochran Freund & Young LLC

(57) ABSTRACT

A *Eucomis* plant particularly distinguished by a plant with a compact and full plant habit, short fragrant pink racemes and having foliage with lanceolate-shaped leaves, is disclosed.

1 Drawing Sheet

Genus and species: *Eucomis vandermerwei*×*Eucomis hybrida.*
Variety denomination: 'GSALIPOL'.

BACKGROUND OF THE NEW PLANT

The present invention comprises a new and distinct variety of *Eucomis*, botanically known as *Eucomis vandermerwei*× *Eucomis hybrida*, and hereinafter referred to by the variety name 'GSALIPOL'. The new variety originated from a cross in Moss Landing, Calif. in May 1997 between the female *Eucomis* parent, an un-named *Eucomis vandermerwei* (un-patented) and the male *Eucomis hybrida* parent, 'Hawkfall Hybrids' (patent status unknown). A single plant selection was subsequently chosen for further evaluation and asexual propagation in Moss Landing, Calif.

The new plant was first asexually propagated in April 2003 in Moss Landing, Calif. and has been asexually reproduced by vegetative cuttings and tissue culture for nine years in Moss Landing, Calif. The present invention has been found to retain its distinctive characteristics through successive asexual propagations by vegetative cuttings and tissue culture.

'GSALIPOL' has not been made publicly available or sold more than one year prior to the filing date of this application.

SUMMARY OF THE INVENTION

The following are the most outstanding and distinguishing characteristics of the new variety when grown under normal horticultural practices in Moss Landing, Calif.

1. A short plant with a compact and full plant habit; and
2. Short and fragrant pink racemes and having foliage with lanceolate-shaped leaves.

DESCRIPTION OF THE PHOTOGRAPH

This new *Eucomis* plant is illustrated by the accompanying photograph which shows the overall plant habit, foliage, buds, and blooms (mature and immature) of the plant. The colors are as true as can be reasonably obtained by conventional photographic procedures. The photograph is of a two-year-old plant grown in a greenhouse in Moss Landing, Calif. in July 2012.

DESCRIPTION OF THE NEW VARIETY

The following detailed descriptions set forth the distinctive characteristics of 'GSALIPOL'. The data which defines these characteristics were collected from asexual reproductions carried out in Moss Landing, Calif. The plant history was taken in June 2012 on two-year old plants based on a 1.75 inch to 2.25 inch-diameter bulb grown in summer greenhouse conditions in Moss Landing, Calif. Color references were taken under natural light and are to The R.H.S. Colour Chart of The Royal Horticultural Society of London (R.H.S.) 2001.

Classification:

*Family.*—Asparagaceae.

*Botanical name.*—*Eucomis vandermerwei*×*Eucomis hybrida.*

*Common name.*—Pineapple Lily.

*Denomination.*—'GSALIPOL'.

Parentage:

*Female.*—An un-named *Eucomis vandermerwei* (un-patented).

*Male.*—*Eucomis hybrida* 'Hawkfall Hybrids' (patent status unknown).

Plant:

*Form.*—Compact with leaves arranged more or less symmetrically below the raceme; the overall effect of the raceme is columnar with a topknot of leaves, somewhat like a pineapple.

*Height above the soil.*—8.0 inches to 11.0 inches for a 1.75 inch to 2.25 inch bulb, depending on the greenhouse conditions.

*Height of top of raceme above the soil.*—8.0 inches to 11.0 inches, depending on growing conditions.

*Diameter of plant.*—15.5 inches to 20.5 inches.

*Blooming period.*—Natural blooming period in the Northern Hemisphere is May through August; as bloom development is day-length neutral, manipulation of bulb harvest timing, storage length, and growing environment allow for year-round blooming.

Leaves:

*Arrangement.*—More or less symmetrical below the racemes; leaves arise from a common base meristem as in a true bulb, where some bulbs in larger sizes have multiple base meristems.

*Quantity (per plant).*—Varies, but 15-25 is typical of a 1.75 inch to 2.25 inch bulb grown under bright greenhouse conditions.

*Width.*—1.25 inches to 1.75 inches.

*Length.*—7.5 inches to 9.5 inches in greenhouse conditions, but shaded plants and larger bulbs have longer leaves.

*Shape.*—Lanceolate.

*Apex.*—Acute.

*Base.*—Contiguous with lanceolate leaf.

*Margin.*—Entire and continuous with a slight undulation of the edge.

*Venation (both surfaces).*—Parallel with a slightly impressed central vein on the upper surface, slightly exposed on lower surface.

*Surface texture.*—Smooth and slightly glossy.

*Color (both upper and lower surfaces).*—RHS 137B (Green).

Topknot:

*Form.*—15-28 miniature leafy bracts atop the raceme and arranged in more or less a symmetrical pattern, radiating from the apex and resembling a pineapple topknot; approximately 0.9 inches to 1.27 inches in height and 0.27 inches to 0.43 inches in diameter.

*Size.*—2.2 inches to 2.8 inches in diameter.

*Color.*—RHS 137B (Green).

Bulb:

*Size.*—1.5 inches to 3.0 inches in diameter.

*Color.*—RHS 200A to RHS 200C (Brown) for the outer leaf scales.

*Shape.*—Non-tunicate.

*Type.*—True bulb.

Raceme:

*Height.*—4.0 inches to 6.5 inches.

*Diameter.*—1.38 inches to 1.5 inches.

*Time to produce a finished flowering plant.*—56-98 days, dependent on post-harvest storage duration and growing conditions.

*Number of flowers per bulb.*—One or more racemes, depending on the bulb size.

*Lastingness of individuals flowers on the plant.*—14 to 28 days.

*Fragrance.*—Present, similar to that of coconut oil.

*Bud.*—Shape: Elliptic. Length: 0.4 inches to 0.5 inches. Width: 0.15 inches to 0.45 inches. Color: A glossy red-purple, RHS 63B to RHS 63C.

*Flower.*—Form: Individual flowers are clustered symmetrically around the top 33% to 50% of one to multiple racemes protruding at or above foliage level even with the foliage; flowers open from the bottom to the top of the stem. Diameter: Individual flowers are 0.8 inches to 1.0 inches when open and clustered around the peduncle or axis. Perianth lobes: Quantity per flower: 6 perianth lobes subtended by size. Color: RHS 65B. Shape: Ovate. Apex: Acute. Base: Broad. Margin: Straight, smooth, and entire. Texture (both surfaces): Smooth.

*Peduncle color.*—RHS 138C (Green).

*Pedicel.*—Length (mean): 6.13 mm. Color: RHS 155B (White).

Reproductive organs:

*Androecium.*—Number of anthers: 6. Filament color: RHS 65B (Red-Purple). Pollen color: RHS 4A (Pale Yellow) to RHS 5B (Ivory). Pollen amount: Slight.

*Gynoecium.*—Pistil number: 1. Pistil length: 0.32 inches to 0.40 inches. Stigma color: RHS 65B (Red-Purple). Style color: RHS 158D to RHS 155D (Yellow-White) from base to tip. Style length: 0.16 inches to 0.23 inches. Style shape: Pyramidal cone.

Fruit and seed set: At maturity, the plant sets a dried, papery, flower-sized pod holding one to multiple seeds. Seeds are ovoid, hard, glossy black (RHS 202 A), and 0.1 inches to 0.2 inches in length.

Disease and insect resistance: Pests and diseases are few; mealybugs can occasionally harbor deep in the bulb scales; *Pythium* can attack roots.

COMPARISON WITH PARENTAL AND COMMERCIAL VARIETIES

'GSALIPOL' differs from the female parent, an un-named *Eucomis vandermerwei* (unpatented), in that blooms of 'GSALIPOL' have a pleasant fragrance similar to that of coconut oil, while blooms of *Eucomis vandermerwei* have a fetid odor. Additionally, the leaves of 'GSALIPOL' do not have any markings, while the leaves of *Eucomis vandermerwei* are covered densely by blackish mauve and russet marks on the upper and lower surfaces of the leaves.

'GSALIPOL' differs from the male parent, *Eucomis hybrida* 'Hawkfall Hybrids' (patent status unknown), in that that blooms of 'GSALIPOL' have a pleasant fragrance similar to that of coconut oil, while blooms of 'Hawkfall Hybrids' have a fetid odor. Additionally, plants of 'GSALIPOL' have more blooms and more leaves than plants of 'Hawkfall Hybrids'.

'GSALIPOL' differs from the commercial comparison, an un-named *Eucomis comosa* (unpatented), in that 'GSALIPOL' has pink flowers, while *E. comosa* has creamy lavender flowers. 'GSALIPOL' has more racemes (3 to 5 times more) than *E. comosa* from the same sized bulb. 'GSALIPOL' has racemes that are half or less than the height produced by *E. comosa.* 'GSALIPOL' has shorter leaves than *E. comosa* (*E. comosa* has leaves that are 1 to 4 times larger). Additionally, 'GSALIPOL' has a more dense and compact plant habit than *E. comosa.*

'GSALIPOL' differs from the commercial comparison, an un-named *Eucomis autumnalis* (unpatented) in that 'GSALIPOL' has pink flowers, while *E. autumnalis* has white flowers. 'GSALIPOL' has a larger number of flowers (25% to 50% to more flowers) than *E. autumnalis* (when produced by similar sized bulbs). The raceme length of 'GSALIPOL' is 25% to 50% shorter than the raceme length of *E. autumnalis.*

I claim:

1. A new and distinct variety of *Eucomis* plant as shown and described herein.

* * * * *

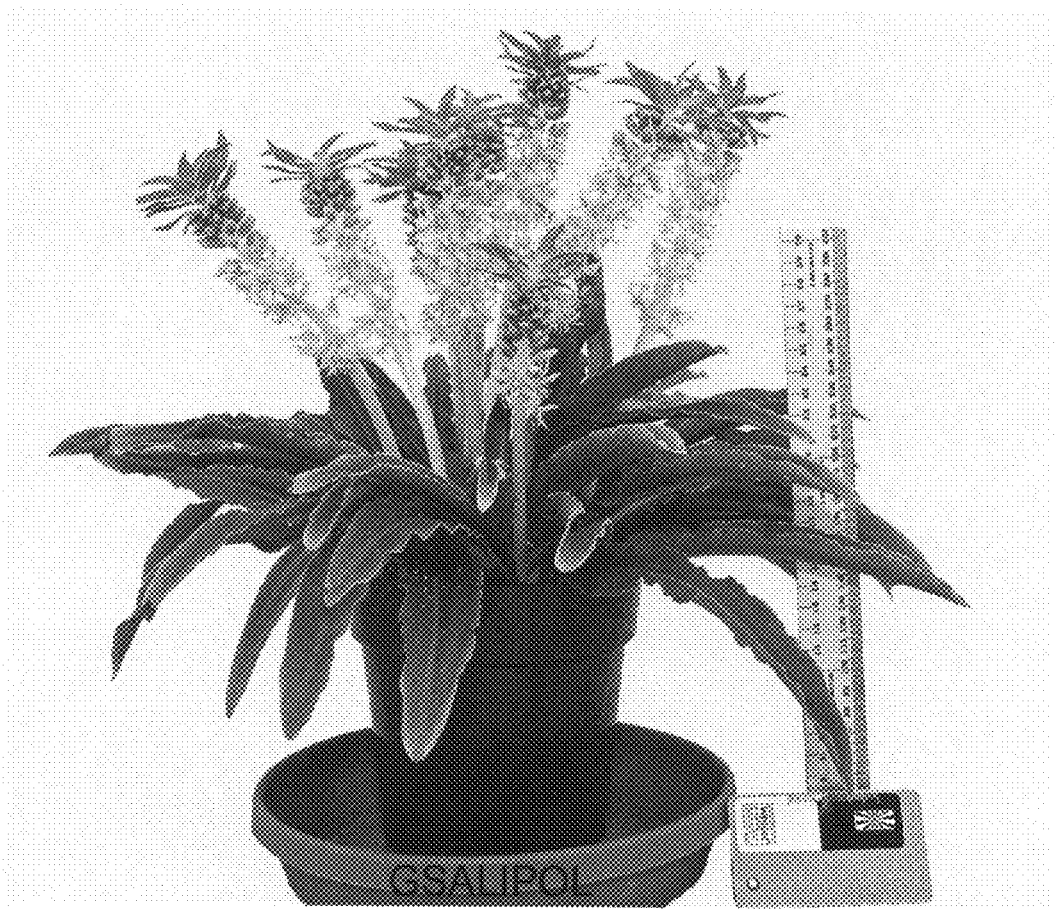
GSALIPOL